(12) United States Patent
Wang et al.

(10) Patent No.: US 11,013,577 B2
(45) Date of Patent: May 25, 2021

(54) NITI ALLOY ROOT CANAL FILE WITH FLEXIBILITY GRADIENT

(71) Applicant: SHENZHEN SUPERLINE TECHNOLOGY CO., LTD, Shenzhen (CN)

(72) Inventors: Zhong Wang, Shenzhen (CN); Jinsong Zhou, Shenzhen (CN)

(73) Assignee: SHENZHEN SUPERLINE TECHNOLOGY CO., LTD, Shenzhen (CN)

( * ) Notice: Subject to any disclaimer, the term of this patent is extended or adjusted under 35 U.S.C. 154(b) by 266 days.

(21) Appl. No.: 16/332,356

(22) PCT Filed: May 27, 2017

(86) PCT No.: PCT/CN2017/086409
§ 371 (c)(1),
(2) Date: Mar. 12, 2019

(87) PCT Pub. No.: WO2018/205319
PCT Pub. Date: Nov. 15, 2018

(65) Prior Publication Data
US 2020/0330187 A1    Oct. 22, 2020

(30) Foreign Application Priority Data

May 9, 2017   (CN) .......................... 201710321938.7

(51) Int. Cl.
*A61C 5/42* (2017.01)
*A61C 5/40* (2017.01)

(52) U.S. Cl.
CPC .................. *A61C 5/42* (2017.02); *A61C 5/40* (2017.02); *A61C 2201/00* (2013.01); *A61C 2201/007* (2013.01)

(58) Field of Classification Search
CPC ....... A61C 5/42; A61C 2201/007; A61C 5/40; A61C 5/55; A61C 5/50; A61C 2201/00;
(Continued)

(56) References Cited

U.S. PATENT DOCUMENTS

| 7,779,542 B2 * | 8/2010 | Aloise | ..................... C22F 1/006 |
| | | | 29/896.11 |
| 8,916,009 B2 * | 12/2014 | Ammon | ................ C22C 38/105 |
| | | | 148/563 |

(Continued)

FOREIGN PATENT DOCUMENTS

| CN | 2655829 Y | 11/2004 |
| CN | 102215772 A | 10/2011 |

(Continued)

OTHER PUBLICATIONS

So-Ram, Oh et al., A comparison of nickel-titanium instruments manufactured using different cross-sectional areas: ability to resist cyclic fatigue, Apr. 2010, vol. 109, Issue 4 (Year: 2010).*

(Continued)

*Primary Examiner* — Cris L. Rodriguez
*Assistant Examiner* — Monea R Grier
(74) *Attorney, Agent, or Firm* — Bayramoglu Law Offices LLC (57) ABSTRACT

A NiTi alloy root canal file with a flexibility gradient includes a tip segment (F1), a middle segment (F2) and a root segment (F3) divided along the axis of the NiTi alloy root canal file with the flexibility gradient. The internal microstructure of the tip segment (F1) of the root canal file is martensite M-phase, the internal microstructure of the middle segment (F2) is R-phase, and the internal microstructure of the root segment (F3) is austenite A-Phase. The present invention further provides a manufacturing method for the NiTi alloy root canal file with the flexibility gradient.

(Continued)

The beneficial effect of the present invention is effectively improving safety in use.

1 Claim, 9 Drawing Sheets

(58) Field of Classification Search
CPC .............. A61L 2400/00; A61L 2400/16; A61L 31/022; C22F 1/004; C22F 1/10; C22F 1/16
USPC ............................................ 433/25, 224, 81
See application file for complete search history.

(56) References Cited

U.S. PATENT DOCUMENTS

| | | | |
|---|---|---|---|
| 10,716,645 B2* | 7/2020 | Aloise | .................. C22C 19/007 |
| 2011/0159458 A1* | 6/2011 | Heath | .................... C22F 1/183 |
| | | | 433/102 |
| 2015/0164617 A1 | 6/2015 | Ammon et al. | |

FOREIGN PATENT DOCUMENTS

| | | |
|---|---|---|
| CN | 105852991 A | 8/2016 |
| WO | 2011143063 A1 | 11/2011 |

OTHER PUBLICATIONS

Shen, Ya et al., Current Challenges and Concepts of the Thermomechanical Treatment of Nickel Titanium Instruments, Feb. 2013 (Year: 2013).*

Choi, JinWook et al., Fracture Resistance of K3 Nickel-Titanium Files Made from Different Thermal Treatments, Nov. 14, 2016 (Year: 2016).*

Gu, Yu et al., Various heat-treated nickel-titanium rotary instruments evaluated in S-shaped simulated resin canals, Mar. 2017, Journal of Dental Sciences, vol. 12, Issue 1, (Year: 2017).*

Qian Xin et. al., Research advance of the surface modification of nickel-titanium instruments and its effect on the property, Chinese Journal of Practical Stomatology, Oct. 31, 2015, vol. 8, No. 10, pp. 634-637.

* cited by examiner

(prior art)

Fig. 3

(prior art)

NITI ALLOY ROOT CANAL FILE WITH FLEXIBILITY GRADIENT

CROSS REFERENCE TO THE RELATED APPLICATIONS

This application is the national phase entry of International Application No. PCT/CN2017/086409, filed on May 27, 2017, which is based upon and claims priority to Chinese Patent Application No. 201710321938.7, filed on May 9, 2017, the entire contents of which are incorporated herein by reference.

TECHNICAL FIELD

The present invention relates to dental instruments, particularly relates to a NiTi alloy root canal file with a flexibility gradient and a manufacturing method thereof in the dental instruments.

BACKGROUND

Root canal files, as the main dental instruments, have the functions of thoroughly cleaning the interior and inner wall of diseased root canals, removing diseased tissues and shaping a complete and smooth inner cavity of root canals.

Figure 1:
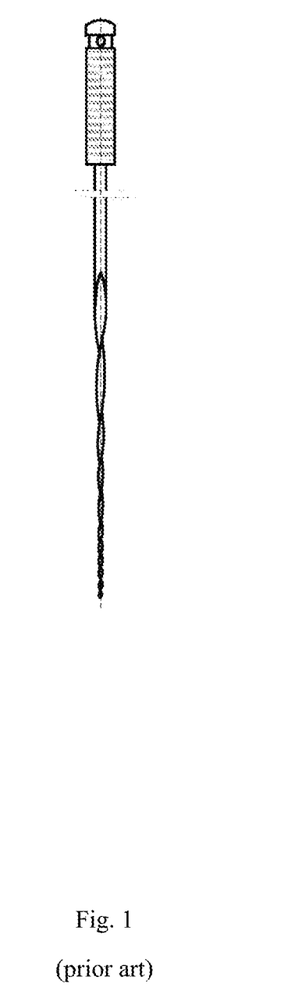
FIG. 1 is a diagram illustrating a structure of a traditional root canal file.

The working segment of a root canal file has a certain cross-section shape, outer contour thereof has a specific coned shape, and is provided with a helical cutting edge, as shown in FIG. 1.

Figure 2:
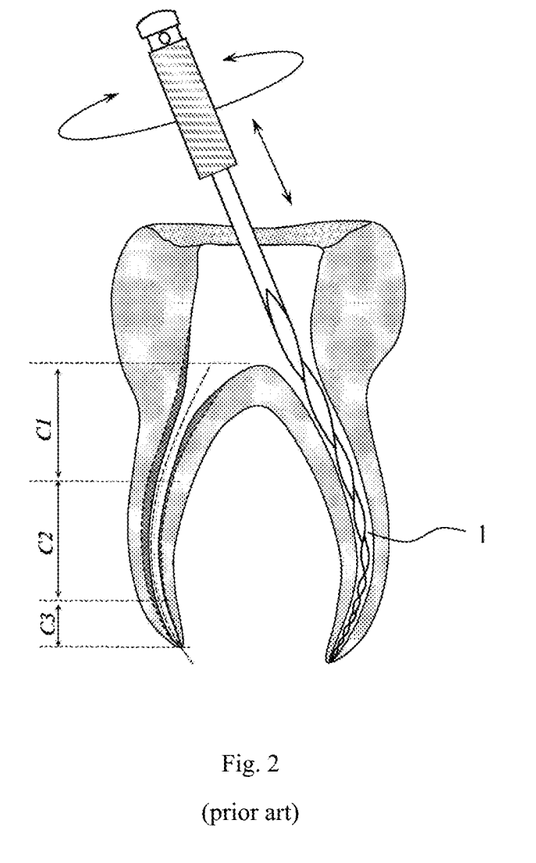
FIG. 2 is a diagram illustrating a working principle of a traditional root canal file.
Figure 3:
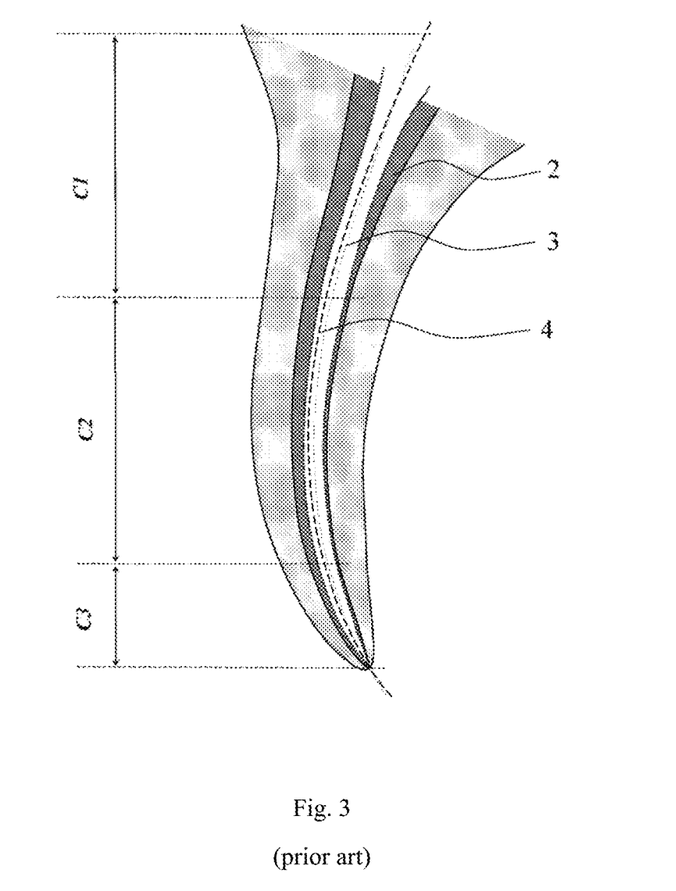
FIG. 3 is a partial enlarged view of FIG. 2.

The root canal file instrument makes a rotary motion in root canal 1 at a certain speed during operation to cut the internal surface of the root canal for the purpose of the root canal cleaning and shaping, as shown in FIG. 2. Since the root canal generally has an inversely conical curved structure, the root canal can be divided into three sections according to its structure, i.e., upper segment C1, middle segment C2, and apical segment C3, and the root canal is curved remarkably in the middle segment C2 and apical segment C3. During the formation of the root canal, the amount of stock removal of the upper segment C1 is maximum, the middle segment C2 has a smaller amount of stock removal than that of the upper segment C1, and the apical segment C3 has the minimum amount of stock removal. FIG. 3 is a partial enlarged view of FIG. 2, in the drawing, 2 is the part that will be cut and removed during the shaping of the root canal, 3 is the axis of the original root canal, and 4 is the axis of the shaped root canal.

To thoroughly clean the interior of the root canal, especially the apical segment C3, the root canal file should be inserted thoroughly into the bottom of the root canal during operation. Due to the constraint of the curved root canal, the root canal file is subjected to high frequency alternating bending deformation during the operation.

In consideration of usability and safety, an ideal root canal file shall meet at least three requirements. Firstly, the root canal file shall have a continuous transitional flexibility to adapt to the curve of the root canal, and to make the tip of the root canal file reach the bottom of the root canal smoothly, so as to clean and shape the apical segment, and meanwhile prevent the generation of steps or lateral perforation on the inner wall of the root canal. Secondly, the root canal file shall have a certain cutting capacity so as to effectively remove diseased tissues and complete root canal shaping. Thirdly, the root canal file shall have a long resistance-to-bending fatigue fracture life to prevent fracture of the root canal file during use and further avoid medical accidents.

Traditional root canal files mainly include stainless steel root canal files and super-elastic NiTi alloy root canal files. The stainless steel root canal file has a good cutting property, but the high rigidity thereof is prone to cause steps and lateral perforation on the inner surface of the root canal, thereby unsatisfying the requirements for the curved root canal.

The NiTi alloy possesses excellent elasticity and good medical and biological properties, and is broadly applied in various medical instruments, including root canal files.

There are three types of phase structure of the microstructure of the NiTi alloy, i.e., austenite A-phase, martensite M-phase, and R-phase, respectively. Diffusionless transformation exists in the NiTi alloy and mutual transformation can occur between the various phases. The NiTi alloy can provide approximately 8% super-elasticity strain when the NiTi alloy is austenite A-phase. This super-elasticity originates from the stress-induced phase transformation between austenite A-phase and martensite M-phase. The NiTi alloy can provide approximately 8% shaping strain when the NiTi alloy is martensite M-phase. This shaping deformation originates from the re-orientation of twin substructure of martensite M-phase. Moreover, the NiTi alloy can provide approximately 1% shaping strain when the NiTi alloy is R-phase, and when continuously performing deformation, approximately 5% super-elasticity strain can be provided. The shaping deformation of R-phase originates from the re-orientation of R-phase substructure, and the super-elasticity strain of R-phase originates from the stress-induced phase transformation between R-phase and martensite M-phase.

Currently, three types of NiTi alloy root canal files are disclosed, which are super-elastic NiTi alloy root canal files, shape memory NiTi alloy root canal files, and segmented root canal files having both super-elasticity and shape memory properties, respectively.

The microstructure of the working segment of the super-elastic NiTi alloy root canal file is fully austenite A-phase under working temperature (human body environment temperature of 37° C.). When the root canal file is bent and deformed under stress during use, stress-induced martensite phase transition occurs inside the root canal file, namely, A to M phase transition. Once the stress is removed, M to A phase transition occurs, and the shape of the root canal file recovers, exhibiting super-elasticity behaviors. Such root canal file has a high strength and an excellent cutting property. However, large deformation resistance is required for elastic bending deformation, thus, it is hard to avoid the serious deviation of the axis of shaped root canal from the axis of the original root canal especially in segment C2. Furthermore, the generation of steps and lateral perforations of the root canal are prone to be caused, especially in segment C3. Besides, the interior microstructure of root canal file repeatedly undergoes periodic phase transition from A to M and from M to A during use. This phase transition process can generate some crystal defects such as dislocation. More and more crystal defects accumulate inside the material as the periodic deformation is repeated, which finally causes the fracture of the root canal file, shortening the resistance-to-bending fatigue life of the super-elastic NiTi alloy root canal file.

The microstructure of the working segment of the shape memory root canal file is fully martensite M-phase under working temperature (37° C.). Such root canal file does not have elasticity, but due to the small bending deformation resistance of shaping deformation, the root canal file is extremely flexible. The deformation mechanism of the root canal file mainly depends on re-orientation of the substructure of M-phase, no crystal defect occurs in the deformation of M-phase, therefore, the resistance-to-bending fatigue life of such root canal file is extremely long. The root canal file with fully martensite M-phase has extremely good flexibility, thus, effectively avoiding the generation of steps and lateral perforation on segment C3 of the root canal during shaping of the root canal. However, since the deformation resistance of M-phase is small, the cutting capacity of such root canal file is very poor, especially, it is difficult to cut segments C1 and C2 of the root canal. Meanwhile, since such root canal file is extremely flexible, distortion deformation along the axis direction easily happens to cause failure of the root canal file, which shortens the working life.

The front segment of the working segment of the segmented root canal file having both super-elasticity and shape memory properties is martensite M-phase, and the rear segment thereof is austenite A-phase under working temperature. The design objective of such root canal file is to endow the front segment with excellent flexibility and bending fatigue fracture resistant property, and endow the rear segment with excellent cutting property. Such an excellent design can effectively avoid the generation of steps and lateral perforation on segment C3 of the root canal, but certain problems still exist. If martensite M-phase segment is too long, though the fatigue life of the front segment of the root canal file is prolonged and the risk of lateral perforation of the root canal is reduced, the cutting efficiency to segment C2 of the root canal is pretty low, and the risk of failure of the root canal caused by axial distortion deformation of the martensite M-phase segment also exists. If martensite M-phase segment is too short, though high efficiency cutting on segments C1 and C2 of the root canal file can be achieved, like the super-elastic root canal file, serious deviation of the axis of the shaped root canal from the axis of the original root canal is easy to be caused, especially on segment C2.

SUMMARY

To solve the problems in the prior art, the present invention provides a NiTi alloy root canal file with a flexibility gradient and a manufacturing method thereof, which effectively improves safety during use.

The present invention provides a NiTi alloy root canal file with a flexibility gradient, including a tip segment, a middle segment and a root segment divided along an axis direction of the NiTi alloy root canal file with the flexibility gradient, wherein the internal microstructure of the tip segment is martensite M-phase, the internal microstructure of the middle segment is R-phase, and the internal microstructure of the root segment is austenite A-phase.

The present invention further provides a manufacturing method for a NiTi alloy root canal file with a flexibility gradient, including the following steps: using a super-elastic NiTi alloy wire with a high content of Ni as a raw material; preparing a root canal file billet of a certain length using the above raw material; treating the root canal file billet in a flexibility gradientization unit to prepare a root canal file billet with a flexibility gradient; machining the root canal file billet with the flexibility gradient to form a root canal file needle with a flexibility gradient; mounting the root canal file needle with the flexibility gradient on a handle to form the NiTi alloy root canal file with the flexibility gradient.

As a further improvement of the present invention, the flexibility gradientization unit includes a heat conductor, an electric heater and a heat insulator, wherein the electric heater is wrapped outside the heat conductor; the heat insulator is wrapped outside the electric heater. A through hole penetrating the heat conductor, the electric heater, and the heat insulator is provided on the center of the flexibility gradientization unit; a limited block is provided beneath the through hole; the diameter of the through hole matches that of the root canal file billet. The root canal file billet is inserted into the through hole to sufficiently contact the heat conductor, and the lower end of the root canal file billet contacts the limited block to guarantee an accurate position where the root canal file billet is heated. A height of the heat conductor is equal to a length of the heating segment of the root canal file billet. Precise control of heating temperature and time of the root canal file billet is realized by adjusting current and time of the electric heater.

The present invention further provides a manufacturing method for a NiTi alloy root canal file with a flexibility gradient, including the following steps: using a super-elastic NiTi alloy wire with a high content of Ni as a raw material; machining to form the root canal file needle, and then inserting the machined root canal file needle into a flexibility gradientization unit for treatment to prepare a root canal file needle with a flexibility gradient; then mounting the root canal file needle on a handle to form the NiTi alloy root canal file with the flexibility gradient.

As a further improvement of the present invention, the flexibility gradientization unit includes a heat conductor, an electric heater and a heat insulator, wherein the electric heater is wrapped outside the heat conductor; the heat insulator is wrapped outside the electric heater. A through hole penetrating the heat conductor, the electric heater, and the heat insulator is provided on the center of the flexibility gradientization unit. A limiting block is provided beneath the through hole; the diameter of the through hole matches that of the root canal file needle. The root canal file needle is inserted into the through hole to sufficiently contact the heat conductor, and the lower end of the root canal file needle contacts the limiting block to guarantee an accurate position where the root canal file needle is heated. A height of the heat conductor is equal to a length of the heating segment of the root canal file needle. Precise control of heating temperature and time of the root canal file needle is realized through adjusting current and time of the electric heater.

Beneficial Effects:

The beneficial effects of the present invention are as follows. Since the tip segment of the NiTi alloy root canal file with the flexibility gradient is relatively flexible and has a good adaptability, the NiTi alloy root canal file with the flexibility gradient can be led to the bottom of the root canal smoothly, effectively preventing the generation of steps and lateral perforation in the tip segment. The middle segment of such NiTi alloy root canal file with the flexibility gradient has a moderate flexibility and a relatively good cutting property, which can effectively shape segment C2 of the root canal and also avoid an excessive deviation of the axis of the shaped root canal from the axis of the original root canal. The root segment of such NiTi alloy root canal file with the flexibility gradient has a good cutting property, which can guarantee efficient shaping of segment C1 of the root canal. Moreover, since the tip segment and the middle segment of the root canal file are respectively martensite M-phase and R-phase, the NiTi alloy root canal file with the flexibility gradient has a good fatigue fracture resistant property, thereby effectively improving safety in use.

DETAILED DESCRIPTION OF THE EMBODIMENTS

The present invention will be further described below in detail in combination with the drawings and specific embodiments.

In public literatures of NiTi alloy root canal files, the super-elasticity of austenite A-phase of the NiTi alloy and shape memory property of martensite M-phase of the NiTi alloy are mainly used, so as to improve practicability and safety of the root canal file.

In fact, R-phase of the NiTi alloy also has an excellent property. As mentioned above, the NiTi alloy can provide approximately 1% shaping strain when the microstructure of the NiTi alloy is R-phase, and continuously performing a deformation, approximately 5% super-elasticity strain can be provided. The super-elasticity originates from the stress-induced phase transition between R-phase and martensite M-phase. The deformation resistance of the super-elasticity generated by R to M phase transition is much lesser than that generated by A to M phase transition. Moreover, the resistance-to-fatigue fracture property of R-phase is also much better than that of austenite A-phase.

Figure 4:
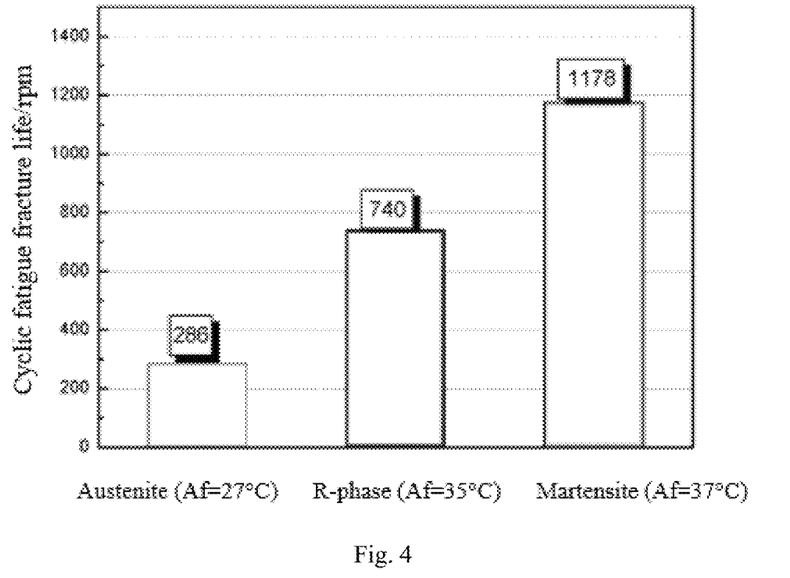
FIG. 4 is a diagram illustrating fatigue fracture lives of a root canal file with A-phase, R-phase, and M-phase.

FIG. 4 illustrates cyclic fatigue fracture lives under a same testing condition of root canal files having a same size after being processed to austenite A-phase, R-phase, and martensite M-phase. The testing condition includes: a bending angle of 45°, a rotational speed of 300 rpm, and a testing temperature of 37° C. As shown in FIG. 4, the fatigue life of the root canal file is relatively short when the microstructure of the root canal file is austenite A-phase; the fatigue life of the root canal file having a microstructure of R-phase is more than 2.5 times longer than that of the root canal file having a microstructure of austenite A-phase; and the fatigue life of the root canal file is the longest when the microstructure of the root canal file is martensite M-phase, which is more than 4 times longer than that of the root canal file having a microstructure of austenite A-phase.

According to defects existing in properties of disclosed NiTi alloy root canal files and features of R-phase of the NiTi alloy, the present invention proposes a NiTi alloy root canal file with a flexibility gradient and a manufacturing method thereof.

Figure 5:
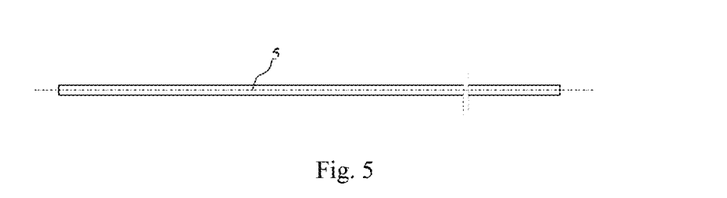
FIG. 5 is a diagram illustrating a root canal file billet in a manufacturing method of a NiTi alloy root canal file with a flexibility gradient of the present invention.
Figure 6:
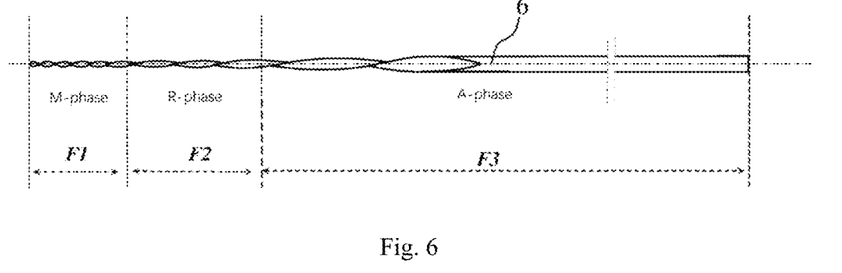
FIG. 6 is a diagram illustrating a root canal file needle of a NiTi alloy root canal file with a flexibility gradient of the present invention.

The present invention relates to a manufacturing method of a NiTi alloy root canal file with a flexibility gradient. The NiTi alloy processed to a super-elastic state is taken as a raw material, and the content of nickel in the alloy should be greater than 50.6 at % Ni (atomic ratio). In order to increase the strength of the alloy, the NiTi alloy should be cold drawn to form a wire with a certain diameter, the amount of deformation of cold drawing should be within the range of 35-45%. The cold drawn alloy wire is then annealed and straightened at 450-600° C. for 30-120 minutes to become root canal file billet 5 that is used for preparing the root canal file with a flexibility gradient, as shown in FIG. 5. The root canal file billet 5 is machined to form a root canal file needle 6 with a flexibility gradient, as shown in FIG. 6. After mounting the root canal file needle 6 with the flexibility gradient on a handle, the root canal file is formed, as shown in FIG. 6.

The present invention relates to a NiTi alloy root canal file with a flexibility gradient. The interiors of various segments have different microstructures under a temperature of 37° C. from the tip segment of the root canal file along the longitudinal direction of the root canal, as shown in FIG. 6. In segment F1 of tip segment of the root canal file, the interior microstructure of the alloy is martensite M-phase. The interior microstructure of segment F2 of middle segment of the root canal file is R-phase. The interior microstructure of segment F3 of root segment of the root canal file is austenite A-phase.

Thus, segment F1 of such NiTi alloy root canal file with a flexibility gradient is relatively flexible and has a good adaptability, which can effectively prevent steps and lateral perforation at the tip segment of the root canal. Segment F2 has a moderate flexibility and a relatively good cutting property, which can avoid an excessive deviation of the axis of the shaped root canal from the axis of the original root canal. Segment F3 has a good cutting property and excellent elasticity, which can guarantee efficient shaping of the root canal. Moreover, since the microstructures of segment F1 and segment F2 of the NiTi alloy root canal file with a flexibility gradient are respectively martensite M-phase and R-phase, the NiTi alloy root canal file with a flexibility gradient has a good resistance-to-fatigue fracture property, thereby effectively improving safety in use.

To realize the root canal file related to the present invention, and make various segments of the root canal file have different phase microstructures, the present invention proposes a flexibility gradientization unit.

Figure 7:
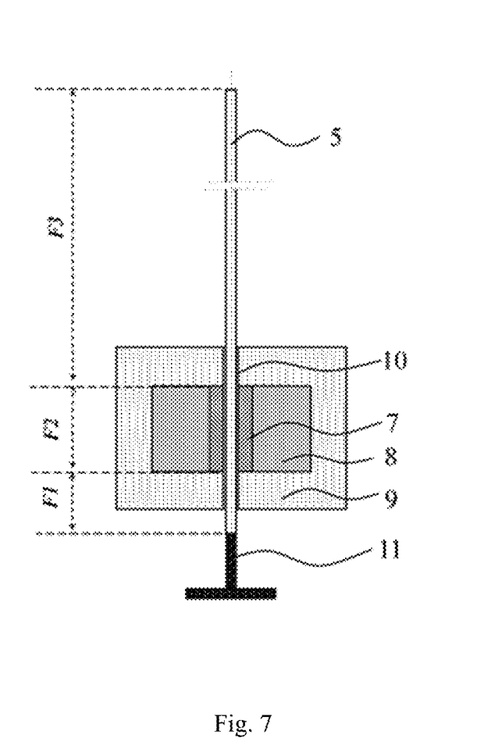
FIG. 7 is a diagram illustrating a cooperation between a root canal file billet and a flexibility gradientization unit in a manufacturing method of a NiTi alloy root canal file with a flexibility gradient of the present invention.
Figure 8:
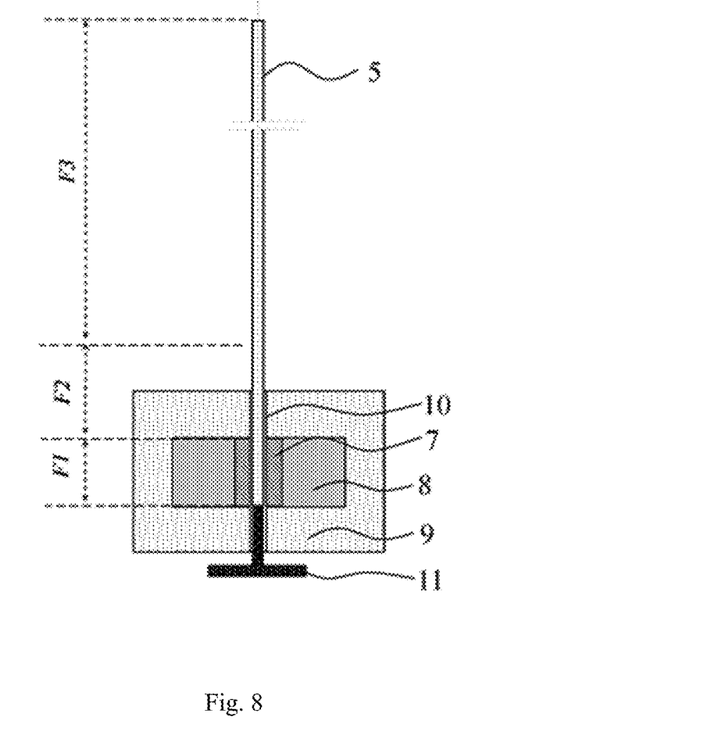
FIG. 8 is a diagram illustrating a cooperation between a root canal file billet and a flexibility gradientization unit in a manufacturing method of a NiTi alloy root canal file with a flexibility gradient of the present invention.

The flexibility gradientization unit includes heat conductor 7, electric heater 8 and heat insulator 9. The electric heater 8 is closely wrapped outside the heat conductor 7, and the heat insulator 9 is wrapped outside the electric heater 8, thus preventing heat loss. The through hole 10 is provided on the center, and limiting block 11 is provided beneath the through hole 10 as shown in FIG. 7 and FIG. 8. The diameter of the through hole 10 matches that of the root canal file billet 5, which makes the root canal file billet 5 sufficiently contact heat conductor 7 after being inserted into the through hole 10. Thus, root canal file billet 5 is guaranteed to be heated. The lower end of root canal file billet 5 contacts the limiting block 11 to guarantee an accurate position where the root canal file billet 5 is heated. The height of heat conductor 7 is equal to the length of the heating segment of root canal file billet 5. Precise control of heating temperature and time of root canal file billet 5 is realized through adjusting current and time of heater 8.

Figure 9:
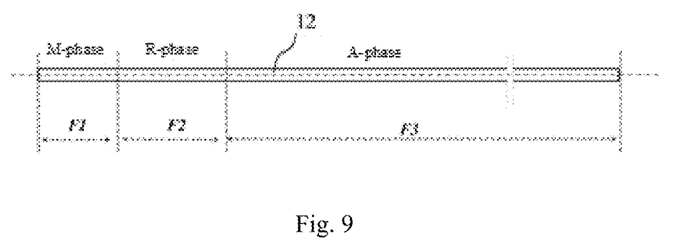
FIG. 9 is a diagram illustrating a root canal file billet after a flexibility gradientization treatment in a manufacturing method of a NiTi alloy root canal file with a flexibility gradient of the present invention.

FIG. 7 is a diagram illustrating segment F2 of the root canal file billet 5 during heating process. The microstructure of segment F2 of the root canal file billet 5 can transform to R-phase through adjusting the heating temperature and time of the heater 8. FIG. 8 is a diagram illustrating segment F1 of the root canal file billet 5 during heating process. The microstructure of segment F1 of the root canal file billet 5 can transform to martensite M-phase through adjusting the heating temperature and time of the heater 8. Thus, NiTi alloy billet 12 having different phase microstructures in various segments is acquired, as shown in FIG. 9.

Figure 10:
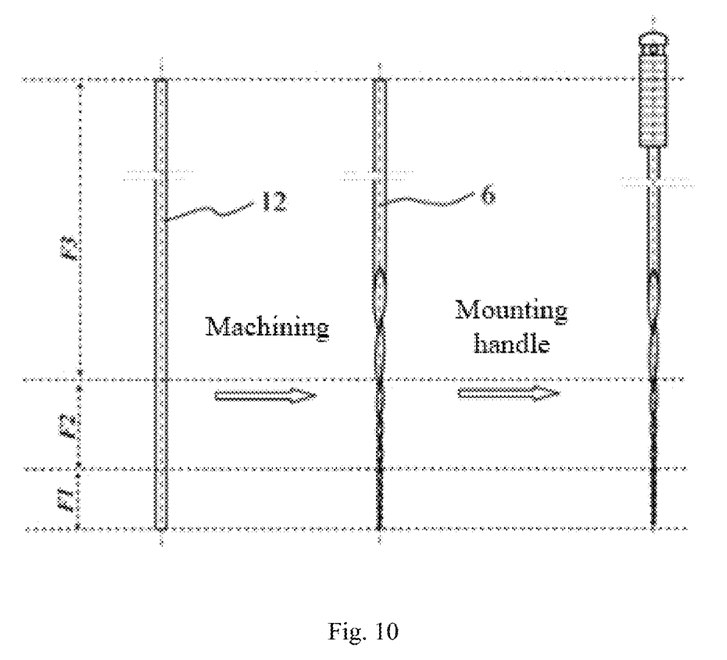
FIG. 10 is a diagram illustrating a root canal file billet, a root canal file needle, and a root canal file in a manufacturing method of a NiTi alloy root canal file with a flexibility gradient of the present invention.

Root canal file needle 6 with a flexibility gradient required is acquired by machining the NiTi alloy billet 12 after various segments are processed, as shown in FIG. 6. Root canal file needle 6 is then mounted on a handle to form the NiTi alloy root canal file with a flexibility gradient of the present invention, the process is shown as FIG. 10.

Figure 11:
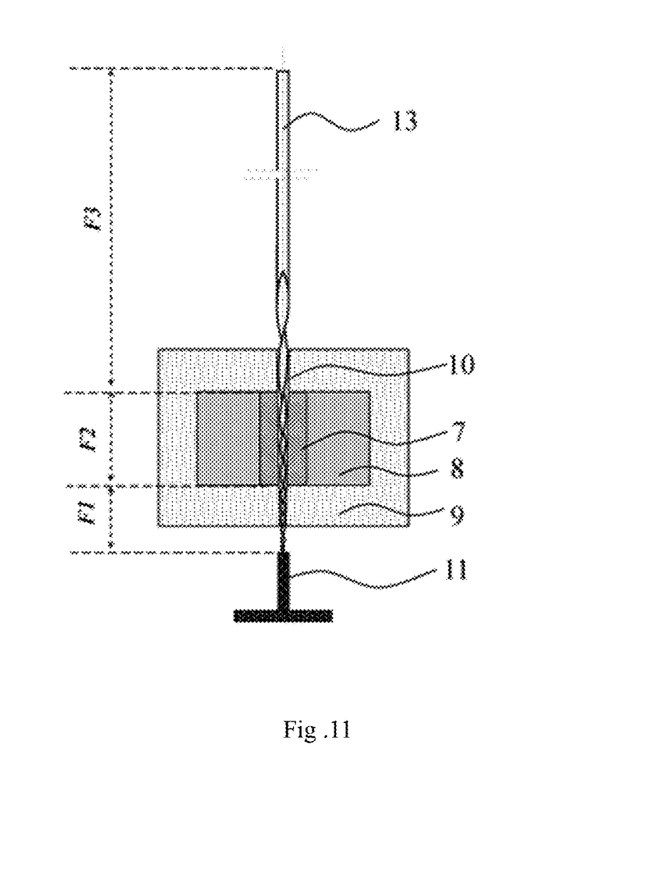
FIG. 11 is a diagram illustrating a cooperation between a root canal file needle and a flexibility gradientization unit in a manufacturing method of a NiTi alloy root canal file with a flexibility gradient of the present invention.
Figure 12:
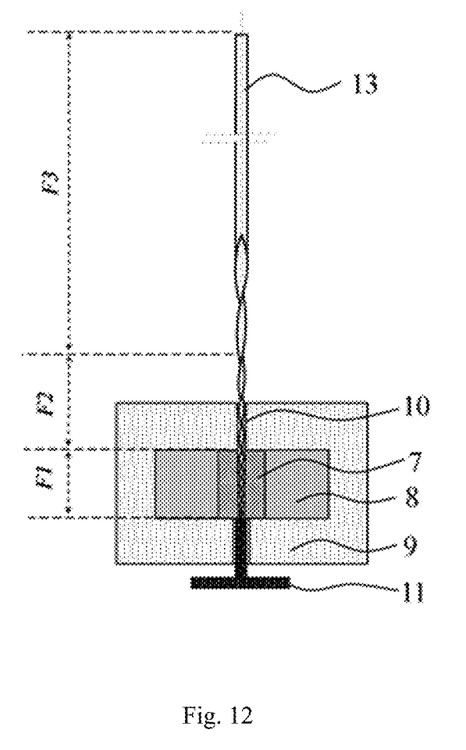
FIG. 12 is a diagram illustrating a cooperation between a root canal file needle and a flexibility gradientization unit in a manufacturing method of a NiTi alloy root canal file with a flexibility gradient of the present invention.

Another manufacturing method of the NiTi alloy root canal file with a flexibility gradient is as follows. Cold drawing is performed on the NiTi alloy with a nickel content of greater than 50.6 at % Ni (atomic ratio) to form a wire with a certain diameter, the amount of deformation of cold drawing should be within the range of 35-45%; annealing and straightening are performed on the cold drawn alloy wire at 450-600° C. for 30-120 minutes, then machining is performed to form the super-elastic root canal file needle 13; and the formed super-elastic root canal file needle 13 is inserted into the through hole 10 of the treatment unit for heat treatment, as shown in FIG. 11 and FIG. 12. Treatment by the unit is performed on the super-elastic root canal file needle 13 to form the root canal file 6 with a flexibility gradient.

FIG. 11 is a diagram illustrating segment F2 of the super-elastic root canal file needle 13 after machining during heating process. The microstructure of segment F2 of the root canal file needle can transform to R-phase through adjusting the heating temperature and time of the heater 8. FIG. 12 is a diagram illustrating segment F1 of the super-elastic root canal file needle 13 after machining during heating process. The microstructure of segment F1 of the root canal file needle can transform to M-phase through adjusting the heating temperature and time of the heater 8. The through hole 10 of the unit can be subjected to profiling to realize a well contact between heat conductor 7 and super-elastic root canal file 13.

The root canal file needle 6 with a flexibility gradient is then mounted on a handle to form the NiTi alloy root canal file with a flexibility gradient of the present invention.

For the NiTi alloy root canal file with flexibility gradient and the manufacturing method thereof provided by the present invention, since the tip segment of the NiTi alloy root canal file with the flexibility gradient is relatively flexible and has a good adaptability, which can lead the NiTi alloy root canal file with the flexibility gradient to the bottom of the root canal smoothly, thus effectively preventing the generation of steps and lateral perforations. The middle segment of such NiTi alloy root canal file with the flexibility gradient has a moderate flexibility and a relatively good cutting property, which can effectively shape segment C2 of the root canal and avoid an excessive deviation of the axis of the shaped root canal from the axis of the original root canal. The root segment of such NiTi alloy root canal file with the flexibility gradient has a good cutting property, which can guarantee efficient shaping of segment C1 of the root canal. Moreover, since the tip segment and the middle segment of the root canal file are respectively martensite M-phase and R-phase, the NiTi alloy root canal file with the flexibility gradient has a good resistance-to-fatigue fracture property, thereby effectively improving safety in use.

The foregoing is further detailed description for the present invention in combination with detailed preferred embodiments, but is not intended to limit detailed embodiments of the present invention. Those skilled in the art can further make a variety of simple deductions or variations without deviating from the principle of the present invention, which should be covered in the protection scope of the present invention.

What is claimed is:

1. A NiTi alloy root canal file with a flexibility gradient, comprising: a tip segment, a middle segment, and a root segment; wherein
    the tip segment, the middle segment, and the root segment are divided along an axis of the NiTi alloy root canal file; and
    the content of nickel in the alloy is greater than 50.6 at % Ni (atomic ratio), so that
    at about 37° C., an internal microstructure of the tip segment is a martensite M-phase, an internal microstructure of the middle segment is a R-phase, and an internal microstructure of the root segment is an austenite A-phase, and a resistance-to-fatigue fracture of the NiTi alloy root canal file resists breakage during use.

* * * * *